US00PP35687P2

(12) United States Plant Patent
Humphreys et al.

(10) Patent No.: US PP35,687 P2
(45) Date of Patent: Mar. 12, 2024

(54) ***HEBE* PLANT NAMED 'HUMDIME'**

(50) Latin Name: ***Hebe* hybrid**
Varietal Denomination: Humdime

(71) Applicants: Stephen Humphreys, Spalding (GB); Yvonne P Humphreys, Spalding (GB)

(72) Inventors: Stephen Humphreys, Spalding (GB); Yvonne P Humphreys, Spalding (GB)

( * ) Notice: Subject to any disclaimer, the term of this patent is extended or adjusted under 35 U.S.C. 154(b) by 0 days.

(21) Appl. No.: 18/223,067

(22) Filed: Jul. 18, 2023

(30) Foreign Application Priority Data

Jul. 26, 2022 (QZ) ..... PBR 20221779

(51) Int. Cl.
*A01H 5/02* (2018.01)
*A01H 6/68* (2018.01)

(52) U.S. Cl.
USPC ..... Plt./226
CPC ..... *A01H 6/68* (2018.05)

(58) Field of Classification Search
USPC ..... Plt./226, 251
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hebe* plant named 'Humdime' that is characterized by its variegated foliage that is creamy yellow in color with a green stripe in the center with the leaves turning mostly all green in the winter under low light conditions, its white flowers, and its height of 15 to 20 cm in its first season in the garden and a height of 60 cm as a mature plant in the garden.

2 Drawing Sheets

Botanical classification: *Hebe* hybrid.
Cultivar designation: 'Humdime'.

CROSS REFERENCE TO A RELATED APPLICATION

This application claims priority to a European plant breeders' rights application filed on Jul. 26, 2022, application No. 2022/1779. The Applicant received the information for the Plant breeders' rights application directly from the Inventors.

BACKGROUND OF THE INVENTION

The present invention relates to a new and distinct *Hebe* plant, botanically of hybrid origin and known as *Hebe* 'Humdime' and will be referred to hereafter by its cultivar name, 'Humdime'. 'Humdime' is an evergreen shrub grown for use as a container plant and as a landscape shrub.

The Inventors discovered the new cultivar in March of 2019 as a naturally occurring branch mutation of *Hebe* 'Wiri Mist' (not patented) that was growing in a trial field in their nursery in Spalding, United Kingdom.

Asexual propagation of the new cultivar was first accomplished by stem cuttings in March of 2019 by one of the Inventors in Spalding, The United Kingdom. Asexual propagation by stem cuttings has determined that the characteristics of the new cultivar are stable and reproduced true to type in successive generations.

SUMMARY OF THE INVENTION

The following traits have been repeatedly observed and represent the characteristics of the new cultivar, which in combination distinguish 'Humdime' as a new and distinct cultivar of *Hebe*.

1. 'Humdime' exhibits variegated foliage that is creamy yellow in color with a green stripe in the center with the leaves turning mostly all green in the winter under low light conditions.
2. 'Humdime' exhibits white flowers.
3. 'Humdime' exhibits a height of 15 to 20 cm in its first season in the garden and a height of 60 cm as a mature plant in the garden.

The parent plant of 'Humdime' differs from 'Humdime' in having young foliage that is non-variegated and light green in color. 'Humdime' can be most closely compared to *Hebe* 'Celebration' (U.S. Plant Pat. No. 28,670) and 'Wiri Charm' (not patented). 'Celebration' is similar to 'Humdime' in foliage coloration. 'Celebration' differs from 'Humdime' in having foliage with early growth under colder temperatures that is tinged red-purple in color on the leaf edges and flowers that are purple-pink in color. 'Wiri Charm' differs from 'Humdime' in having flowers that are lavender to pale violet in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Genesis Plant Marketing, Nigel Judd, Neil Alcock, Horticulture Week, Garden Centre Association/Chester, LinkedIn, Twitter, Floral Daily, Christopher Collins, New Plant Awards, Wyevale Nurseries, Facebook, Muck Rack, Horticulture Trade Association, and Herefordshire & Worcestershire Chamber of Commerce.

BRIEF DESCRIPTION OF THE DRAWINGS

The accompanying color photographs illustrate the overall appearance and distinct characteristics of the new *Hebe*. The photographs were taken of an 18-month-old plant of 'Humdime' as grown in an unheated greenhouse in a 13-cm container in IJsselstein, The Netherlands.

The photograph in FIG. 1 is a side view of 'Humdime' in bloom.

Figure 1:
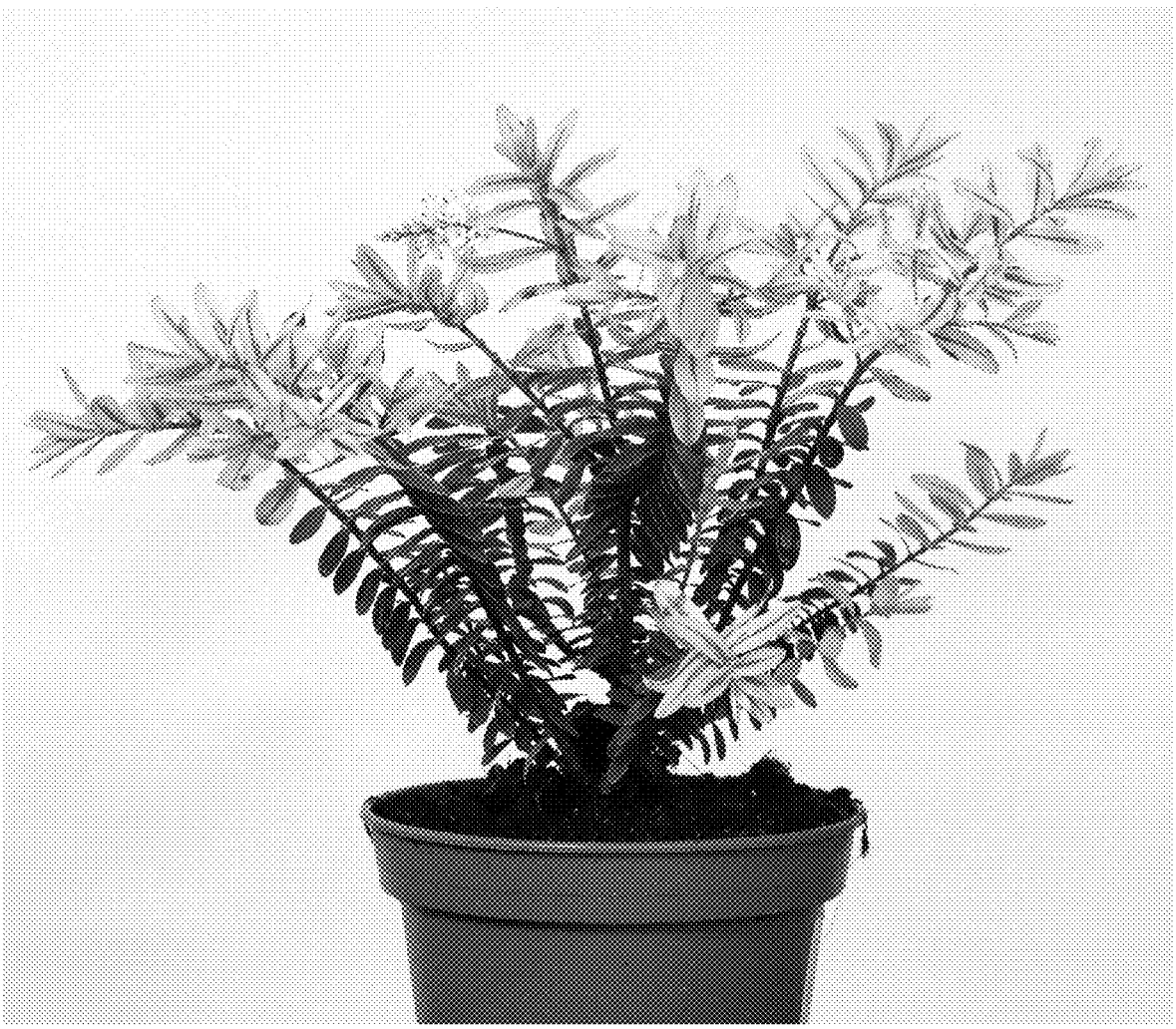
Figure 2:
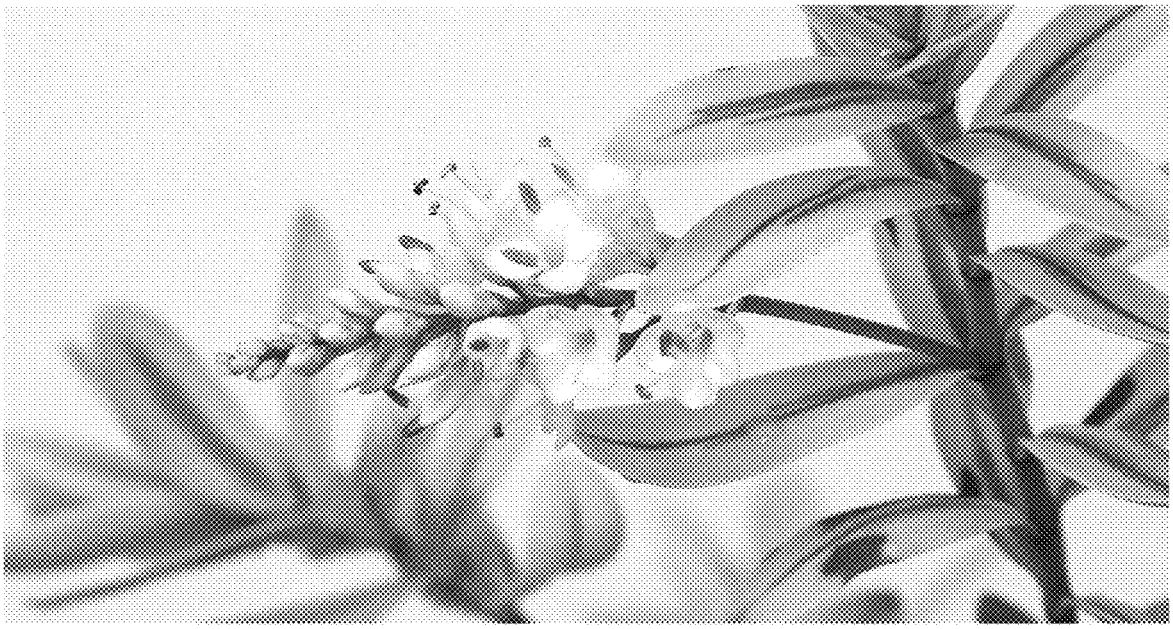

The photograph in FIG. 2 provides a close-up view of an inflorescence of 'Humdime'.

Figure 3:
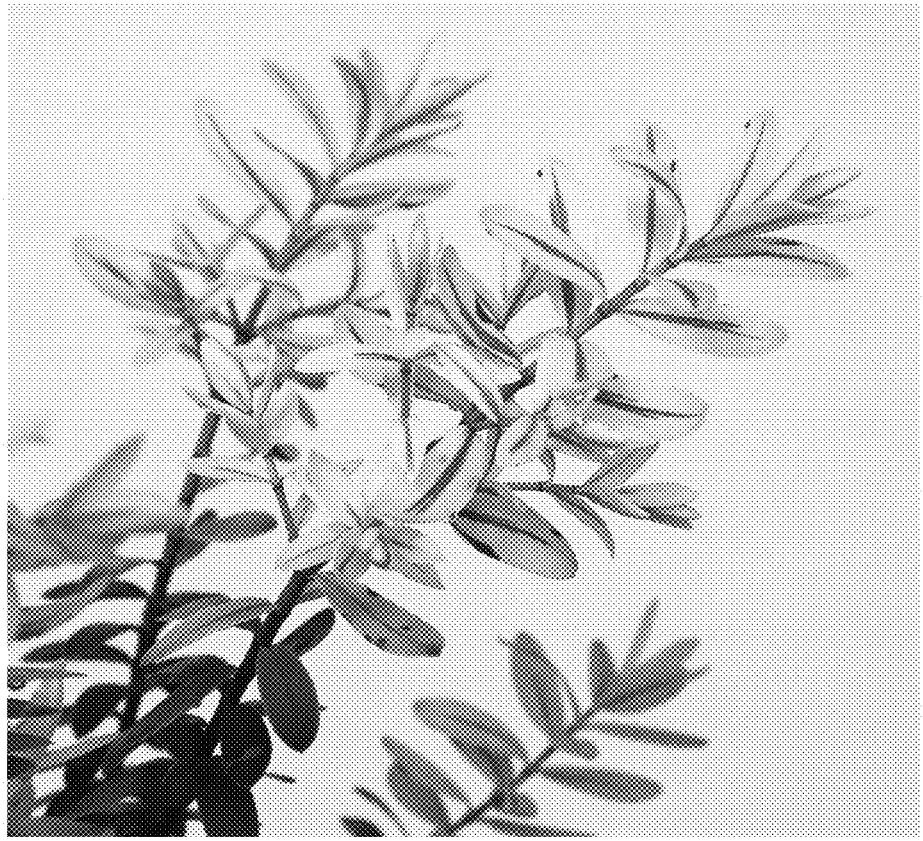

The photograph in FIG. 3 provides a close-up view of the foliage of 'Humdime'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 18-month-old plants of the new cultivar as grown in an unheated greenhouse in 13-cm containers in IJsselstein, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—An average of 5 weeks from late April through the first week of June, in The United Kingdom.

*Plant type*.—Evergreen shrub.

*Plant habit*.—Compact, upright and spreading.

*Height and spread*.—Average of 60 cm in height, 29 cm in width as a mature plant in the garden.

*Hardiness*.—At least in U.S.D.A. Zones 8 to 11.

*Diseases and pests*.—No susceptibility or resistance to diseases or pests has been observed.

*Root description*.—Fibrous to slightly fleshy.

*Propagation*.—Softwood stem cuttings.

*Root development*.—2 weeks to initiate roots and 6 weeks to produce a young rooted plant from a rooted cutting.

*Growth rate*.—Moderate.

Branch description:

*Branch size*.—Lateral branches are an average of 16.8 cm in length and 2.25 mm in diameter.

*Branch shape*.—Round.

*Branch color*.—Young; 146C, internodes; N199A and 199B, mature; 148A.

*Branch surface*.—Slightly glossy, densely covered with very short glandular hairs, 0.1 mm in length, matches surface color.

*Branch strength*.—Strong.

*Internode length*.—Average of 7.5 mm.

*Branching habit*.—Held in an average angle of 45° to vertical.

*Branching quantity*.—Main; 10, lateral per main branch; 4.

Foliage description:

*Leaf shape*.—Elliptic to narrowly obovate.

*Leaf division*.—Single.

*Leaf base*.—Cuneate.

*Leaf apex*.—Bluntly acute.

*Leaf venation*.—Pinnate, upper surface; 146B, lower surface; N189B.

*Leaf margins*.—Entire.

*Leaf attachment*.—Petiolate.

*Leaf arrangement*.—Opposite.

*Leaf surface*.—Both surfaces smooth, glabrous, upper surface very slightly glossy, lower surface matte.

*Leaf color*.—Young upper surface; 5C, with an irregular narrow axillary central band (area adjacent to main vein) and occasional small spots on lamina and along the margins NN137C, young lower surface; 5C, but slightly lighter, with an irregular narrow axillary central band (area adjacent to main vein) and occasional small spots on lamina and along the margins N138B, mature upper surface; NN137B, mature lower surface; a blend of 137B and 146A.

*Leaf number*.—Average of 48 per lateral branch.

*Leaf size*.—An average of 2.6 cm in length and 9 mm in width.

*Petioles*.—Flattened in shape, diameter at widest point 3 mm, diameter at narrowest point 0.5 mm, 1 mm in length, both surfaces are smooth, glabrous and very slightly glossy, strong, upper surface color 144B, lower surface color 144A.

Flower description:

*Inflorescence type*.—Raceme.

*Inflorescence size*.—Average of 3.6 cm in height and 2.1 cm in width.

*Inflorescence lastingness*.—About 7 days, self-cleaning.

*Flower shape*.—Campanulate.

*Flower fragrance*.—None.

*Flower quantity*.—Average of 34 flowers per inflorescence.

*Flower arrangement*.—Axillary racemes.

*Flower aspect*.—Outward.

*Flower size*.—Average of 8 mm in height, 7.5 mm in diameter, 1 cm in depth, throat diameter 1.5 mm, flower tube 4 mm in length and 2 mm in diameter.

*Peduncles*.—Strong strength, 5.3 cm in length and about 1.25 mm in diameter, 146B in color, held at about a 50° angle to lateral branch, surface is matte and densely covered with very short glandular hairs an average of 0.1 mm in length, matches surface color.

*Pedicels*.—Moderately strong, average of 3 mm in length and 0.5 mm in diameter, held at about a 30° angle to peduncle, 176B in color.

*Flower buds*.—Oblong, 5 mm in length and 2 mm in diameter, surface is matte, color; NN155D, immature calyx 145D, flushed green at the tip 143B, upper (sunny) side tinged 181D.

*Calyx*.—Rotate-shaped, average of 3.5 mm in length and 2.5 mm in diameter.

*Sepals*.—4, 1 whorl, lower sepals; 3.5 mm in length, upper sepals; 3 mm in length, lower and upper sepals 1 mm in width, narrowly obovate to nearly oblong in shape, entire margins, arrangement; rotate, acute tip, base cuneate and fused, surfaces dull and smooth, color: when opening upper surface; 145D and lighter, top flushed with 143C, when opening lower surface; 145D, top flushed with 143B, upper sepals tinged 181D, fully open upper surface; 145D and lighter, top flushed with 143C, fully open lower surface; 145D, top flushed with 143B.

*Petals.*—4, 1 whorl, obovate in shape, bottom 52.5% fused, average of 7.5 mm in length and 3.5 mm in width, entire and slightly involute margins, apex obtuse, upper and lower surface is smooth and glabrous, non-rugose, upper surface very slightly glossy, slightly velvety, lower surface matte and velvety, color: upper and lower surface when opening and fully open NN155D, veins 157D to NN155D.

*Bracts.*—A single bract is placed below each individual flower, narrow ovate in shape, narrow obtuse apex, cuneate base, 3 mm in length, 1 mm in width, both surfaces glabrous, color; 145D, flushed 143C at the tip.

Reproductive organs:

*Gynoecium.*—Pistil; 1, 8 mm in length, stigma; club-shaped, 5 mm in length, too small to measure color, style; 7.95 mm in length and NN15D in color, ovary; 144C in color.

*Androecium.*—Stamens; 2, anthers; oblong, dorsifixed in shape, 2.5 mm in length, 1 mm in width and N77B in color, filaments; 8 mm in length, 4 mm implanted into side of tube, color; NN155D, pollen; low in quantity, 156A in color.

*Fruit and seed.*—None observed to date.

It is claimed:

1. A new and distinct cultivar of *Hebe* plant named 'Humdime' as herein illustrated and described.

* * * * *